(12) United States Patent
Emerson

(10) Patent No.: US 7,674,388 B2
(45) Date of Patent: Mar. 9, 2010

(54) PHOTOPOLYMER SERUM SEPARATOR

(75) Inventor: Jane F. Emerson, Irvine, CA (US)

(73) Assignee: The Regents of the University of California

( * ) Notice: Subject to any disclaimer, the term of this patent is extended or adjusted under 35 U.S.C. 154(b) by 216 days.

(21) Appl. No.: 11/499,436

(22) Filed: Aug. 4, 2006

(65) Prior Publication Data

US 2007/0187341 A1    Aug. 16, 2007

Related U.S. Application Data

(60) Provisional application No. 60/707,299, filed on Aug. 10, 2005.

(51) Int. Cl.
*B01D 21/26* (2006.01)
*B01D 12/00* (2006.01)

(52) U.S. Cl. .................. 210/789; 210/781; 210/782; 210/516; 210/511; 210/518; 252/60; 422/101; 422/102; 435/2

(58) Field of Classification Search .......... 210/781, 210/782, 516, 789, 511, 518; 525/444; 252/60; 422/101, 102; 435/2
See application file for complete search history.

(56) References Cited

U.S. PATENT DOCUMENTS

| 3,647,070 | A |   | 3/1972  | Adler |     |
|-----------|---|---|---------|-------|-----|
| 3,780,935 | A |   | 12/1973 | Lukacs et al. | |
| 3,920,557 | A |   | 11/1975 | Ayres |     |
| 4,101,422 | A |   | 7/1978  | Lamont et al. | |
| 4,235,725 | A |   | 11/1980 | Semersky | |
| 4,946,601 | A | * | 8/1990  | Fiehler ........................ 210/782 |
| 5,266,199 | A |   | 11/1993 | Tsukagoshi et al. | |
| 5,582,954 | A | * | 12/1996 | Swatton et al. ........... 430/281.1 |
| 6,248,844 | B1|   | 6/2001  | Gates et al. | |
| 6,361,700 | B2|   | 3/2002  | Gates et al. | |
| 6,565,968 | B1| * | 5/2003  | Li et al. ....................... 428/343 |
| 2006/0160025 | A1| | 7/2006 | Lungu | |
| 2007/0003588 | A1|*| 1/2007 | Chinn et al. ................. 424/423 |
| 2007/0005024 | A1|*| 1/2007 | Weber et al. ................ 604/265 |
| 2007/0020629 | A1| | 1/2007 | Ross et al. | |
| 2007/0187341 | A1| | 8/2007 | Emerson | |

FOREIGN PATENT DOCUMENTS

| EP | 0520185 | 12/1992 |
| EP | 0705882 | 4/1996 |
| EP | 0744026 | 11/1996 |
| EP | 0928301 | 7/1999 |

OTHER PUBLICATIONS

Definition of solid from Websters dictionary retrieved from Internet on Jul. 7, 2009 at <http://lionreference.chadwyck.com/searchFulltext.do?id=33051427&idType=offset&divLevel=2&queryId=../session/1246981509_23137&area=mwd&forward=refshelf&trail=refshelf>.*

* cited by examiner

*Primary Examiner*—Krishnan S Menon
*Assistant Examiner*—Marjorie Christian
(74) *Attorney, Agent, or Firm*—Fish & Associates PC

(57) ABSTRACT

Contemplated whole blood separators tubes include a curable composition with a density intermediate to the density of serum and the cell-containing fraction. After centrifugation, the curable composition is located between the serum and the cell-containing fraction and preferably irradiated with UV light to initiate a curing reaction in which the curable composition solidifies to a barrier that is immobilized and resistant to breakdown at freezing temperatures and extended storage.

15 Claims, 2 Drawing Sheets

US 7,674,388 B2

PHOTOPOLYMER SERUM SEPARATOR

This application claims priority to U.S. provisional application Ser. No. 60/707,299 filed Aug. 10, 2005.

FIELD OF THE INVENTION

The field of the invention is serum separation, and especially to serum separation using a polymerizable composition that forms a barrier between the separated phases.

BACKGROUND OF THE INVENTION

Among other sample manipulations, blood separation is a routine process that is typically required in many analytic tests. Most commonly, separation is carried out in a centrifuge using a polymeric gel having a density (about 1.04) that is between the heavier cell-containing phase and the lighter serum-containing phase. Examples for separation devices that use intermediate density polymers are found in U.S. Pat. No. 3,647,070 where polymer spheres form the barrier layer, while U.S. Pat. No. 5,266,199 describes a tube-and-ball valve that controls separation of the serum from the cell-containing phase. However, such barriers are often either incomplete and tend to leak, or impracticable for various reasons.

Alternatively, relatively impervious silicone-containing barrier layers can be used in the serum separation as described in U.S. Pat. No. 3,780,935, and drug-impermeable separation polymers are described in EP 0 928 301 in which fluid polymers are used as a barrier layers. Similarly, U.S. Pat. No. 4,235,725 describes the use of polybutadiene plus filler material as a barrier forming material. Such barrier materials often provide at least some advantage, but typically fail to maintain the separation over a prolonged period. In still further known serum separation devices, high-density polymers can be employed for blood separation in which the density is adjusted to a desirable degree with a density reducing component as taught in EP 0 705 882. Such compositions are often highly compatible with blood, and often exhibit favorable viscosity. However, such barrier layers are often unstable over prolonged periods. Alternatively, the viscosity of the intermediate polymer may also be increased in the separator tube by photopolymerization before the tubes is used for collection and separation as described, for example, in U.S. Pat. No. 6,361,700 or U.S. Pat. No. 6,248,844. Once more, while such tubes often provide increased sample stability, the barrier layer is typically unstable over prolonged periods and will deteriorate upon freezing.

Still further known devices and methods are described in EP 0 520 185 using fatty acid amides admixed with a gel, and EP 0 744 026 in which a peripheral water swellable band is taught as a barrier forming means. U.S. Pat. No. 3,920,557 described use of beads coated with an adhesive to form a barrier layer between the serum and the cell containing phase, while U.S. Pat. No. 4,101,422 discloses copolyesters with specific molecular weight and viscosity as barrier-forming compositions. While such known compositions tend to maintain the separation over at least relatively short periods, the separation layers are often not sufficiently stable to allow reliable storage over several days or while frozen.

Therefore, while numerous compositions and methods for centrifugal serum separation are known in the art, all or almost all of them suffer from one or more disadvantages. Thus, there is still a need to provide improved composition and methods to improve serum separation devices.

SUMMARY OF THE INVENTION

The present invention is directed to devices and methods for serum separator tubes that include a curable composition with an intermediate density to thereby locate between the serum fraction and the cell-containing fraction after centrifugation. Once separation of the phases is achieved, the curable composition is then subjected to conditions effective to solidify, crosslink, or otherwise strengthen the barrier formed by the curable composition.

Therefore, in one aspect of the inventive subject matter, a serum separator tube comprises a curable composition that is formulated to have a density between an average density of a serum fraction of whole blood and a cell-containing fraction of whole blood, and that is formulated to be mixable with or flowable in whole blood. Most typically, the composition will comprise a plurality of reactive groups in an amount effective to form a crosslinked composition upon initiation of crosslinking, wherein the crosslinked composition is impermeable to the cell-containing fraction of whole blood.

The curable composition in some preferred aspects is flowable and optionally thixotropic and will most preferably comprise a polymer (e.g., polyisoprene, polyester, polyacrylate, and/or silicone oil). Such polymers will typically include a reactive group (e.g., as pendant or terminal group) to allow formation of the crosslinked composition using a photo-initiated radical reaction. The photoinitiated reaction may proceed directly without a photoinitiator, or may require a one or more photoinitiators. Irradiation is preferably performed with UV light. Alternatively, it is contemplated that the crosslinked composition may also be crosslinked in a reaction using a radical starter (e.g., chemically or thermally activated).

Consequently, in another aspect of the inventive subject matter, a method of separating whole blood into a serum fraction and a cell-containing fraction includes a step of providing a collection tube that contains a curable composition and mixing whole blood with the curable composition, wherein the curable composition has a density between an average density of the serum fraction and the cell-containing fraction. The sample is then spun at a centrifugal force sufficient to separate the serum fraction and the cell-containing fraction such that the curable composition forms a barrier layer between the serum fraction and the cell-containing fraction, and in yet another step, the curable composition is cured after centrifugation.

Various objects, features, aspects and advantages of the present invention will become more apparent from the following detailed description of preferred embodiments of the invention.

DETAILED DESCRIPTION

The inventor has discovered that serum separation can be significantly improved using a polymeric barrier material that is cured after the material has settled in a position between the lighter serum and the heavier cell-containing phase. Most preferably, it is contemplated that the remaining components and methods of serum separation remain as currently practiced.

Figure 1A:
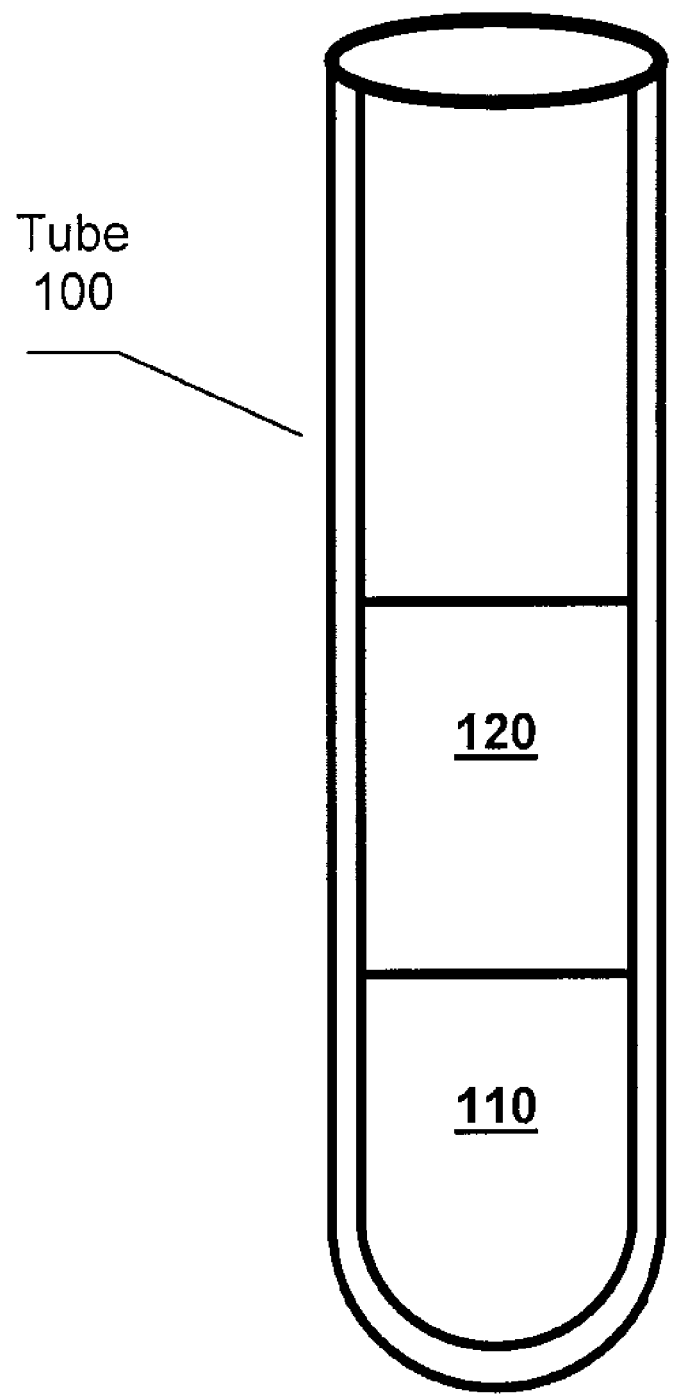
FIG. 1A is a schematic of a serum tube before centrifugation.

In one exemplary aspect of the inventive subject matter, as shown in FIG. 1A, a serum separator tube 100 comprises an evacuated and sterile glass or plastic tube (e.g., similar or identical to VACUTAINER™ tubes (Franklin Lakes, NJ USA 07417)) having a removable top with a portion that can be pierced to receive the blood 120. The curable material 110 forming the barrier layer is preferably a biocompatible organic polymer with a density of between about 1.04-1.06 g/cm$^3$, and most preferably 1.04 g/cm$^3$. Preferred polymers comprise a polyester backbone similar to those described in U.S. Pat. Nos. 6,361,700 and 6,248,844, both of which are incorporated by reference herein. Polymerization is preferably carried out to achieve the desired density of between about 1.04-1.06 g/cm$^3$. However, and in contrast to the methods and compositions provided in the '700 and '844 patent, polymerization is not run to completion but stopped using a polymerization terminator (e.g., using radical quenchers, catalyst complexing agent, etc.) in a minimum amount effective to stop further polymerization.

Figure 1B:
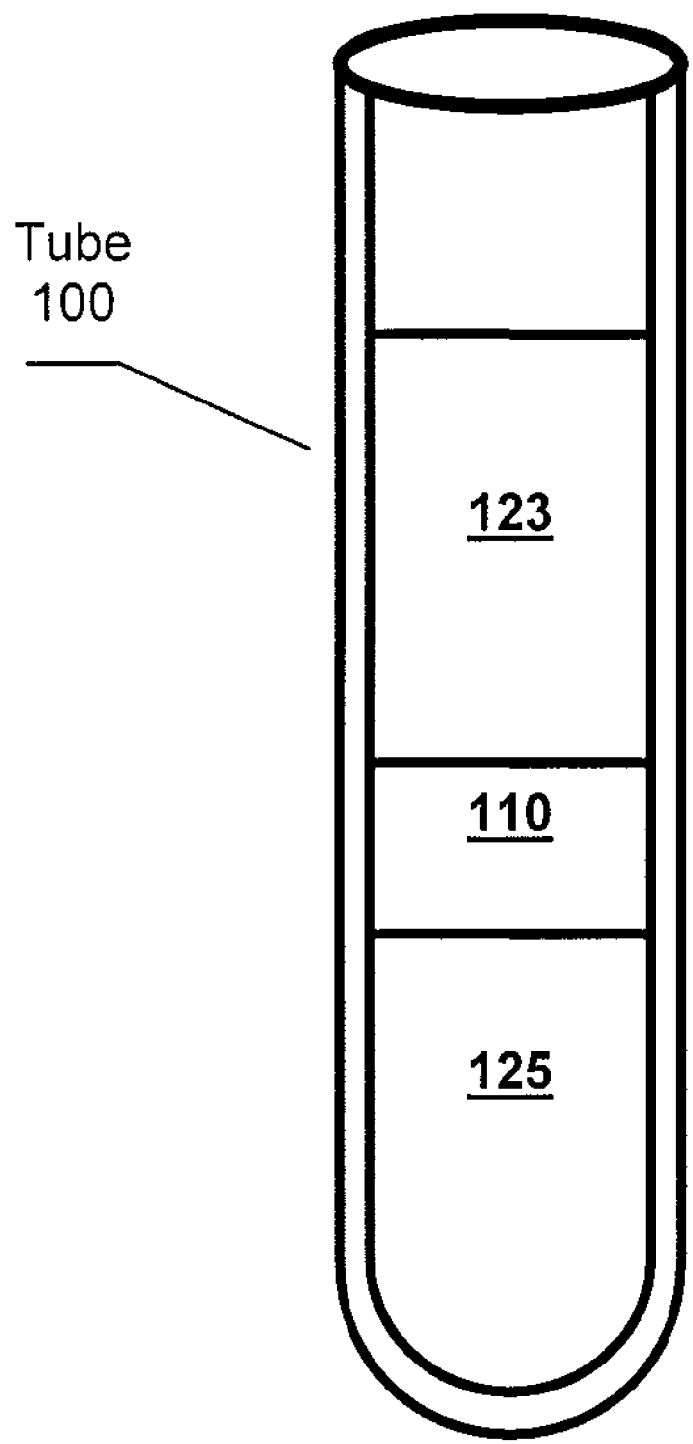
FIG. 1B is a schematic of the serum tube of FIG. 1A after centrifugation.

As the sample contacts the incompletely cured polymer (the curable composition), it is contemplated that the polymerization terminator is diluted to a concentration that allows the polymerization to be re-initiated. Prior to re-initiation, the whole blood sample is separated in the container by centrifugation as shown in FIG 1B, which will leave the cell-containing fraction 125 in the bottom portion of the container 100 and the serum fraction 123 in the upper portion of the container, wherein both fractions are separated by the incompletely cured polymer 110. Most preferably, re-initiation of polymerization may be assisted by irradiating the polymer with UV light or other high-energy source. Thus, it should be appreciated that the polymeric is additionally cured after the separation is completed and the so separated serum can then be accessed without contamination of a pipette, decanted, or even frozen. Moreover, it should be recognized that the final cured barrier layer is substantially permanent (i.e., stable over several days, or even weeks).

While it is generally preferred that the separator tubes include a polyester polymer, it should be noted that the exact nature of the polymeric material is not limiting to the inventive subject matter, and that numerous alternative polymers are also suitable. Indeed all known polymers suitable for blood separation are deemed appropriate for use herein, including silicon oil, polyamides, olefinic polymers, polyacrylates polyesters and copolymers thereof, polysilanes, and polyisoprenes. To achieve a desired initial density (typically between about 1.03 and 1.05), it is contemplated that the density may be adjusted by virtue of molecular composition, as well as by inclusion of appropriate filler material (e.g., silica, latex, or other inert material). For example, suitable polymeric materials are described in U.S. Pat. Nos. 3,647,070, 3,920,557, or 3,780,935, or in EP 0 928 301 or 0 705 882, which are incorporated by reference herein. Furthermore, it is contemplated that the serum separators may include additional materials and/or reagents to achieve a desired purpose. For example, the separators presented herein may include EDTA, heparin, citrate, dextrose, etc. It should be noted that the term "serum" is used herein to also include plasma, and other substantially cell free fluids derived from whole blood.

Depending on the particular material, it is contemplated that the mode and/or mechanism of polymerization to the separator polymer may vary considerably, and all know manners of polymerization are deemed suitable for use herein. For example, contemplated polymerizations include various radical or cationic polymerizations (e.g., using photolabile compounds, radical startes, etc.), condensation polymerizations, esterifications, amide formation, etc. Thus, reactive groups will especially include acid groups (and most preferably mono- and dicarboxylic groups), conjugated diene groups, aromatic vinyl groups, and alkyl(meth)acrylate. Such exemplary reactive groups and reaction conditions are described, for example, in U.S. Pat. No. 6,989,226, which is incorporated by reference herein. It should furthermore be appreciated that the reactive groups can be coupled to the terminus of a polymer as end groups as described in WO 99/64931, which is incorporated by reference herein, or that the reactive groups may be provided as pendant groups (e.g., as described in U.S. Pat. No. 5,336,736, incorporated by reference herein).

It is generally preferred that polymerization is fully supported by reactive groups on polymer, but additional reagents may also be suitable, including radical starters, including those described in U.S. Pat. Nos. 5,582,954, 4,894,315, and 4,460,675, which are incorporated by reference herein. Additionally contemplated compositions also include those that provide a crosslinking group to the polymer such that the polymer has reactive groups that react with a bifunctional crosslinker (e.g., ethylenically unsaturated compounds) to thereby form crosslinked polymers.

Thus, in another aspect of the inventive subject matter, a first polymerization may be performed to form the barrier material, and a second polymerization reaction or curing reaction employs a reaction that involves one or more reactive groups in the barrier polymer to harden/solidify the barrier. For example, where the barrier polymer is a polyester, curing of the polymer may be performed using a radical polymerization reaction that includes peroxo-, photolabile, or redox starters to generate a radical species that initiates the curing reaction between reactive groups (ethylenically unsaturated groups, epoxy groups, etc.) of polymeric strands of the polyester. Alternatively, catalyzed CLICK chemistry or other reactions may be employed so long as such reactions do not interfere with a downstream analytic process, and/or so long as the barrier polymer is curable to a degree that allows decanting and/or freezing without loss of separation.

In other aspects of the inventive subject matter, the polymerization reaction to form the barrier polymer may be incomplete (e.g., by addition of polymerization terminator, or depletion of reactive substrate) and the so formed barrier material can be cured after the barrier has formed by re-initiation of proper reaction condition. For example, where the concentration of the polymerization terminator has fallen below an inhibitory level via dilution with blood, polymerization may be started by UV irradiation. Alternatively, and depending on the particular curing mechanism, addition of reactive materials and/or crosslinkers may also be suitable. Further polymers and reactive groups suitable for photopolymerization are described in U.S. Pat. No. 5,086,138, which is incorporated by reference herein.

Thus, specific embodiments and applications of curable serum separator barrier materials have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A serum separator tube containing a blood separator composition comprising:
   a curable composition disposed within the tube, and that is formulated to have a density between an average density of a serum fraction of whole blood and a cell-containing fraction of whole blood, and that is further formulated to be mixable with or flowable in whole blood before curing, and to be solid and immobilized after curing;
   wherein the curable composition comprises a flowable polymerizable compound formed from polymerizing a first portion of a plurality of reactive groups of the curable composition, and having a second portion of the plurality of reactive groups in an amount effective to form a solid, immobilized crosslinked composition upon initiation of crosslinking through curing the curable composition; and
   wherein the curable composition forms a barrier between the fractions due to separation, and upon curing forms the crosslinked composition in a manner where the barrier becomes solid, immobilized, and impermeable to the cell-containing fraction of whole blood.

2. The serum separator tube of claim 1 wherein the curable composition is flowable and optionally thixotropic.

3. The serum separator tube of claim 2 wherein the curable composition comprises a polymer selected from the group consisting of a polyisoprene, a polyester, an acrylate, and a silicone oil.

4. The separator tube of claim 1 wherein the curable composition comprises a polymer and wherein the reactive groups in the polymer are selected to allow formation of the crosslinked composition using a photo-initiated radical reaction.

5. The separator tube of claim 4 wherein the reactive group is activated by UV irradiation.

6. The separator tube of claim 1 wherein the curable composition comprises a polymer and wherein the reactive groups in the polymer are selected to allow formation of the crosslinked composition using a radical starter.

7. The separator tube of claim 6 wherein the reactive group is activated by a radical starter that is chemically activated.

8. A method of separating whole blood into a serum fraction and a cell-containing fraction using a collection tube and a blood separator composition, comprising:
   providing a collection tube that contains a curable composition and mixing whole blood with the curable composition;
   wherein the curable composition is formulated to have a density between an average density of the serum fraction and the cell-containing fraction and to be mixable with or flowable in whole blood before curing, and solid and immobilized after curing, and comprises a polymerizable compound having a plurality of reactive groups in an amount effective to form a solid, immobilized crosslinked composition upon initiation of crosslinking through curing the curable compound;
   centrifuging the sample at a centrifugal force sufficient to separate the serum fraction and the cell-containing fraction such that the curable composition forms a barrier layer between the serum fraction and the cell-containing fraction; and
   curing the curable composition after the step of centrifuging causing the barrier to become solid and immobilized through forming the solid crosslinked composition.

9. The method of claim 8 wherein the curable composition is flowable and optionally thixotropic.

10. The method of claim 9 wherein the curable composition comprises a polymer selected from the group consisting of a polyisoprene, a polyester, an acrylate, and a silicone oil.

11. The method of claim 8 wherein the curable composition comprises a polymer and wherein the reactive groups in the polymer are selected to allow formation of the crosslinked composition using a photo-initiated radical reaction.

12. The method of claim 11 wherein the reactive group is activated by UV irradiation.

13. The method of claim 8 wherein the curable composition comprises a polymer and wherein the reactive groups in the polymer are selected to allow formation of the crosslinked composition using a radical starter.

14. The method of claim 13 wherein the reactive group is activated by a radical starter that is chemically activated.

15. A serum separator tube containing a blood separator composition comprising:
   a curable composition disposed within the tube, and that is formulated to have a density between an average density of a serum fraction of whole blood and a cell-containing fraction of whole blood, and that is further formulated to be mixable with or flowable in whole blood before curing, and to be solid and immobilized after curing;
   wherein the curable composition comprises a polymerizable compound having a plurality of reactive groups in an amount effective to form a solid, immobilized crosslinked composition upon initiation of crosslinking through curing the curable composition; and
   wherein the curable composition forms a barrier between the fractions due to separation, and upon curing in the presence of the fractions forms the crosslinked composition in a manner where the barrier becomes solid, immobilized, and impermeable to the cell-containing fraction of whole.

* * * * *